(12) United States Patent
De Rosa et al.

(10) Patent No.: US 6,410,036 B1
(45) Date of Patent: Jun. 25, 2002

(54) EUTECTIC MIXTURES IN COSMETIC COMPOSITIONS

(75) Inventors: Mario De Rosa; Mose Rossi, both of Naples (IT)

(73) Assignee: E-L Management Corp., New York, NY (US)

( * ) Notice: Subject to any disclaimer, the term of this patent is extended or adjusted under 35 U.S.C. 154(b) by 0 days.

(21) Appl. No.: 09/564,218

(22) Filed: May 4, 2000

(51) Int. Cl.⁷ .................................................. A61K 7/00
(52) U.S. Cl. ...................................................... 424/401
(58) Field of Search ......................................... 424/401

(56) References Cited

U.S. PATENT DOCUMENTS

| | | | |
|---|---|---|---|
| 5,932,229 A | * 8/1999 | Ptchelintsev et al. | ....... 424/401 |
| 5,989,528 A | * 11/1999 | Tanner et al. | .................. 424/59 |

FOREIGN PATENT DOCUMENTS

| | | | |
|---|---|---|---|
| EP | 074701 | 12/1996 | .......... A61K/47/48 |
| WO | WO9926617 | 6/1999 | .......... A61K/31/19 |
| WO | WO0015179 | 3/2000 | ............ A61K/7/00 |
| WO | WO0015202 | 3/2000 | .......... A61K/31/00 |
| WO | WO0033877 | 6/2000 | .......... A61K/47/00 |

\* cited by examiner

*Primary Examiner*—Jose' G. Dees
*Assistant Examiner*—Konata M. George
(74) *Attorney, Agent, or Firm*—Karen A. Lowney, Esq.

(57) ABSTRACT

The present invention relates to a liquid, substantially anhydrous eutectic mixture comprising a principal acid component, such as a hydroxy acid, and at least one other component selected from the group consisting of a carbohydrate, a polyol, an amino acid, and a carboxylic acid. The mixtures remain liquid at room temperature, are relatively non-irritating, and can be used to deliver higher levels of the principal acid than would ordinarily be possible. The invention also provides a method of making such a mixture comprising heating the component having the lowest melting point to the temperature at which it melts, dissolving the remaining component or components in the melted component, and allowing the mixture to cool.

33 Claims, No Drawings

EUTECTIC MIXTURES IN COSMETIC COMPOSITIONS

FIELD OF THE INVENTION

The invention relates to cosmetic compositions. More specifically, the invention relates to cosmetic compositions containing relatively high levels of active components that cause substantially no irritation to the skin.

BACKGROUND OF THE INVENTION

The presence of biologically active ingredients in cosmetics has become commonplace today. Such materials provide the consumer with considerable benefits, such as exfoliation, lightening of abnormal pigmentation, lipid barrier repair, and the like, in addition to the more traditional benefits of moisturizing. With the biological benefits, however, sometimes comes the problem of irritation. While most potential users can readily appreciate the advantages of these materials with no problem, certain active ingredients can cause discomfort to individuals with particularly sensitive skin, thereby depriving that segment of the population of the benefits of these products.

One of the most common groups of compounds to which a certain segment of the population reacts is acids, particularly hydroxy acids, or retinoic acid, which have provided enormous benefits to those who are not sensitive to them. These compounds are highly effective keratolytic agents, that effectively bring about exfoliation of dead keratinocytes, reducing the appearance of fine lines and wrinkles, and conferring a smooth, glowing look to the facial skin. However, because of the possibility of irritation, particularly at higher concentrations, these compounds have not reached their full potential in cosmetic compositions, generally having to be used at lower levels than would be optimum for activity. Thus, there continues to be a need for formulations that will permit the exploitation of these compounds to their fullest potential. The present invention fulfills such a need.

SUMMARY OF THE INVENTION

The present invention relates to eutectic mixtures of a principal acid component and at least one other component selected from the group consisting of a carbohydrate, a polyol, a carbonylic compound, an amino acid, and a carboxylic acid. The mixtures of the invention are used in anhydrous cosmetic compositions that, when applied to the skin, slowly release the acid in the presence of the skin's moisture, thereby obtaining the benefit of the acid substantially without any irritation. The invention also relates to a method for preparing a eutectic mixture of an acid component and at least one other component selected from the group consisting of a carbohydrate, a polyol, a carbonylic compound, an amino acid, or a carboxylic acid, the method comprising heating the component having the lowest melting point to the temperature at which it melts, dissolving the remaining component or components in the melted component, and allowing the mixture to cool. While the components of the mixtures are solid before combination, when heated and dissolved as described, they remain as a homogeneous liquid when returned to room temperature.

DETAILED DESCRIPTION OF THE INVENTION

The mixtures of the invention provide a non-irritating base for delivery of potentially irritating acids. The mixtures are non-aqueous, so that the acidic character of the acid component, which is only realized in an aqueous environment, is not present in the mixture. In essence, the acid component cannot ionize, so remains undissociated in the mixture, until the mixture is exposed to the moisture of the skin, at which time it is slowly converted to the acid form and released to the skin to provide the benefits achieved by such acids. The mixtures of the invention are referred to as "eutectic mixtures" which for purposes of the present application and claims means an equilibrium phase between two or more components, which equilibrium phase, or mixture, does not have any of the physical characteristics of the individual components. Eutectic mixtures are known in various chemical areas are known, but are ordinarily difficult to create, and to the best of the inventors' knowledge, have not previously been used in cosmetics or pharmaceuticals.

It has now been unexpectedly discovered that it is possible to create such cosmetically and pharmaceutically acceptable eutectic mixtures with biologically active acid components, when they are combined with specified other components under certain conditions. In the present case, the components of the mixture are all solid at room temperature prior to creation of the mixture, but after melting and dissolution of the components, an anhydrous solution results which remains liquid at room temperature without crystallization of the individual components. This is all achieved, in most cases, in the absence of any additional solvent that dissolves both compounds. To be successfully combined, the individual components must be compatible, i.e., each compound must form an intermolecular interaction with the other, so that this interaction will counteract the usual forces that tend to arrange the individual components into their individual crystalline forms. This result is only obtainable, however, when the components are mixed on the molecular level. In the present mixtures, while not wishing to be bound by any particular theory, it is believed that a complex forms between the two or more components, due to hydrogen bonds, or Van der Waals interactions, between the solutes, interfering with each compound's ability to recrystallize, i.e., to return to the solid state, thereby resulting in a liquid mixture of two normally solid compounds at room temperature. Since this is preferably achieved in the absence of the usual solvent, i.e., water, or at least after the removal of water from the mixture, the mixture is substantially anhydrous, and therefore does not produce the ionization conditions needed to release $H^+$ ions.

It will be recognized that the term "acid" in the present specification and claims is used, for convenience, to refer to both the non-ionized, substantially inert structural acid in the initial mixture, as well as the active, dissociated molecule that exists when the mixture contacts moisture on the skin. The acid that constitutes the principal acid component (referred to as "principal" to distinguish it from the second component which in some cases may also be an acid) of the mixture can be any pharmaceutically or cosmetically acceptable acid, and is preferably one that exhibits some type of biological activity on the skin. Examples of useful acids for the present purpose include, but are not limited to, alpha hydroxy acids, such as glycolic acid, lactic acid, citric acid, malic acid, tartronic acid, tartaric acid, beta hydroxy acids, such as salicylic acid, and retinoic acid.

The second component which forms part of the mixture is a component selected from the group consisting of a carbohydrate, a polyol, a carbonylic compound, an amino acid, and a carboxylic acid. Compounds from each of these groups have been shown to form the desired type of mixture with acids, and while not wishing to be bound by any particular theory, it is believed that, while chemically diverse, compounds in these groups all have the ability to form intermolecular hydrogen bonds, which provide a solvent-type environment conducive to retaining the liquid state of the mixture upon cooling. Examples of useful carbohydrates include, but are not limited to, monosaccharides, such as glucose, galactose and fructose; disaccharides, such as saccharose, lactose, maltose, and trehalose; and polysaccharides, such as low molecular weight dextrins, soluble starch, amylopectin and amylose. Preferably, the polysaccharides are selected from those having no more than twenty carbohydrate units. Polyols, such as sorbitol, 1-thiosorbitol, inositol, mannitol, and polyvinyl alcohol, can also be employed. The second component can also be a carbonylic compound, for example, ketones or aldehydes, such as dihydroxyacetone or erythrulose, or any amino acid(natural or synthetic), for example, glycine, alanine, valine, norvaline, leucine, norleucine, aspartic acid, glutamic aci, asparagine, glutamine, arginine, lysine, serine, threonine, proline, tyrosine, cysteine, cystine, methionine, phenylalanine, histidine, tryptophan, dihydroxyphenylalanine, and methionine, as well as a small peptide, such as a reduced glutathione. The second component can be another acid component such as a carboxylic acid. Examples of carboxylic acids include the alpha and beta hydroxy acids noted above, as well as oxalic, malonic, succinic or mercaptosuccinic, or glutaric acid.

The mixtures are prepared relatively simply. The chosen component having the lowest melting point is heated, with conventional systems or microwaves, to that temperature. When the first component is liquified, the second component (s) can be mixed in and dissolved in the melted first component. It will be understood that the combining of the components can take place before the melting of the first component, and the second component simply blended in when the first component is liquefied, or the second component can be added to the first after the first has been melted. Once the components are dissolved, the resulting mixture is transparent and homogeneous; upon cooling, the mixture retains its liquid nature and transparent, homogeneous appearance. The mixtures will only solidify, without crystallizing, at very low temperatures, e.g., below 0° C., at which point they form transparent solid glasses. The solidification and melting process can be repeated indefinitely.

The foregoing method can be applied to all combinations in which the components are thermostable, i.e. stable at the lowest melting point of a component. In a case in which one or more components are not heat-stable, it is possible to conduct the heating step in the presence of an auxiliary solvent, such as water, or any other solvent with a suitably low boiling point. The solutes are dissolved in the solvent, then the solvent removed by evaporation at reduced pressure, leaving a liquid phase containing only solutes.

For a successful creation of a eutectic mixture, certain ranges of the components must be employed. As a general rule, the principal acid component will be used in an amount between about 40 to about 95% by weight of the mixture, more preferably between about 50 to about 90%. The actual amount of principal acid used will depend upon the identity of the second component. As a general rule, the amount of principle acid employed will be at the lower end of this range when the second component is one having functional groups capable of forming large numbers of hydrogen bonds, for example, for example, mono- and disaccharides. In contrast, the amount of principle acid used will increase as the molecular weight of the second component increases, for example, with soluble starch or polyvinyl alcohol.

It will be recognized that more than one of each type of component can be used in the mixture. A particularly preferred combination is a mixture containing at least one hydroxy acid, preferably an alpha hydroxy acid, and a carbohydrate. A preferred carbohydrate in such a combination is a disaccharide, most preferably the disaccharide trehalose. The latter is a particularly preferred choice because of its own beneficial effects on the skin, particularly its well-established ability to protect biological structures. Mixtures of this type can be used in exfoliation of the skin, reduction of the appearance of lines and wrinkles, and any other therapeutic purpose for which these acids are ordinarily used. The advantage of these mixtures is that much higher levels of acid, for example as high as 85–90%, can be used, thereby increasing their efficacy, while still remaining substantially non-irritating or at least significantly less irritating than a comparable mixture containing water. In fact, mixtures of this type, containing no water, or even an amount of water less than about 5%, does not have a measurable pH, showing the low level of acidity. However, once on the skin, over a period of time, the mixture will effectively achieve the desired exfoliation or other beneficial effect with little or no adverse effect.

The mixtures of the present invention can be used directly on the skin, but more frequently will be employed in a pharmaceutically or cosmetically acceptable carrier. The form may be a cream, lotion, gel, mousse, or the like. Preferably, the formulation contains substantially no water, and in any case, should contain no more than 5% water. The mixture can simply be added to the carrier in an amount sufficient to give the desired concentration of acid in the final formula. Because of the relative safety of the mixtures, however, the range of concentration of the acid can be much higher than in an ordinary acid-in-water-containing formulation; therefore, the amount of acid in the final formulation may be as high as about 70% by weight, and as low as about 0.01%. The actual amounts used in the final formulation will depend upon the intended end use, for example, higher levels of acid will be used to accomplish a chemical peel, whereas lower levels can be used to achieve gentle exfoliation and wrinkle reduction. Because the irritation level of these compositions is so low, however, it is possible to use the acid at a higher level than would normally be used for its intended purpose, and at the same time reduce the frequency of application. For example a composition containing a 70:30 glycolic acid:trehalose mixture can be applied to achieve exfoliation, substantially without causing any erythema.

The mixtures of the invention can also be combined with other actives, and in fact certain actives may be enhanced by their combination within the mixture per se. Examples of actives that may benefit by combination with or within the mixture are self-tanning agents such as DHA or imidazole or erythrulose, or whitening agents/tyrosinase inhibitors, such as kojic acid, licorice extract and components thereof, or arbutin, or resveratrol and its derivatives.

The invention will be further illustrated by the following non-limiting examples.

EXAMPLES

Example 1

This example illustrates the preparation of a glycolic acid/carbohydrate solutions. Solutions of glycolic acid and mono- or polysaccharides are prepared, using different concentrations of components, by melting the glycolic acid component at 85° C. using conventional heating methods. In the liquid glycolic acid, the selected carbohydrate is dissolved. The liquid solution is cooled to room temperature and its chemical and physical characteristics are analyzed. The results are as follows:
(a) glycolic acid/glucose: Solutions are prepared containing from 50% to 70% by weight of glycolic acid. At concentrations of glycolic acid over 70%, metastable solutions that tend to crystallize are obtained; below 50%, an amorphous solid is obtained. For the stable solutions, the viscosity decreases as the concentration of the acid increases. At 25° C., the viscosity of the 60% solution is over 8000 cps.
(b) glycolic acid/trehalose: Solutions are prepared containing from 50% to 70% by weight of glycolic acid. At concentrations over 70% acid, a metastable solution that tends to crystallize is formed and below 50%, an amorphous solid is obtained. The viscosities of the stable solutions are as follows: 50%, >8000 cps; 60%, 8000 cps; 70%, 6000 cps.
(c) glycolic acid/starch: Solutions are prepared containing from 75 to 90% by weight of glycolic acid. In excess of 90%, a metastable solution that tends to crystallize is obtained, and below 75%, an amorphous solid is obtained. Viscosities of stable solutions are as follows: 75%, 6800 cps; 80%, 3450 cps; 90%, 1,200 cps.

Example 2

This example illustrates solutions made with glycolic acid and polyols. The solutions are prepared as described in Example 1. The results are as follows:
(a) glycolic acid/sorbitol: Concentrations of glycolic acid ranging from 40 to 90% are used. In excess of 90%, a metastable solution that tends to crystallize is obtained, and below 75%, an amorphous solid is obtained. Viscosities of stable solutions are as follows: 50%, >8000 cps; 70%, 2000 cps; 85%, 1500 cps; 90%, 800 cps.
(b) glycolic acid/polyvinyl alcohol: Concentrations of between 90–95% by weight of glycolic acid are used, in combination with either 25 or 75 KDa polyvinyl alcohol. Viscous stable solutions result at these concentrations. Over 95% acid, a metastable solution that tends to crystallize is obtained, and below 90%, an amorphous solid is obtained. The viscosity of the solutions decreases as the concentration and molecular weight of the polyvinyl alcohol decreases.

Example 3

This example illustrates the preparation of glycolic acid/hydroxyacid solutions. The solutions are prepared as described in Example 1. The results are as follows:
(a) glycolic acid/tartaric acid: Solutions are prepared containing from 50 to 90% by weight of glycolic acid. At concentrations over 90% acid, a metastable solution that tends to crystallize is formed and below 50%, an amorphous solid is obtained. The viscosities of the stable solutions are as follows: 60%, >8000 cps; 70%, 6500 cps; 80%, 3000 cps, 90%, 1,100 cps.
(b) glycolic acid/citric acid: Solutions are prepared containing from 40 to 90% by weight of glycolic acid. At concentrations over 90% acid, a metastable solution that tends to crystallize is formed and below 40%, an amorphous solid is obtained. The viscosities of the stable solutions are as follows: 50%, >8000 cps; 70%, 4100 cps; 80%, 2000 cps; 90%, 850 cps.

Example 4

This example illustrates the preparation of glycolic acid/carboxylic acid solutions. The solutions are prepared as described in Example 1. The results are as follows:
(a) glycolic acid/2-mercaptosuccinic acid: Solutions are prepared containing from 80 to 95% by weight of glycolic acid. At concentrations over 95% acid, a metastable solution that tends to crystallize is formed and below 80%, an amorphous solid is obtained. In the stability range, the viscosity is about 600 cps.

Example 5

This example illustrates the preparation of glycolic acid/amino acid solutions. The solutions are prepared as described in Example 1. The results are as follows:
Solutions of 80% glycolic acid and various L-amino acids are prepared. The viscosities of the stable solutions depend upon the identity of the amino acid: glycine, 6000 cps; alanine, 5800 cps; valine, 5500 cps; methionine, 1700 cps; glutamic acid, 300 cps; arginine, 8700 cps; asparagine, 1200 cps.

Example 6

This example illustrates the preparation of solutions containing glycolic acid and DHA. DHA has a melting point of about 80° C. The solutions are prepared as described in Example 1. The chemical and physical properties are then analyzed. The results are as follows:
the viscosity at 25° C. of DHA/glycolic acid (10:90) is 1150 cps.

What we claim is:

1. A liquid, substantially anhydrous eutectic mixture comprising a principal acid component and at least one other component selected from the group consisting of a carbohydrate, a polyol, a carbonylic compound, an amino acid, and a carboxylic acid.

2. The mixture of claim 1 in which the principal acid is selected from the group consisting of an alpha hydroxy acid, a beta hydroxy acid, and retinoic acid.

3. The mixture of claim 1 in which the other component comprises a carbohydrate.

4. The mixture of claim 3 in which the carbohydrate is selected from the group consisting of monosaccharides, disaccharides, and polysaccharides.

5. The mixture of claim 1 which comprises an alpha hydroxy acid as the principal acid, and a carbohydrate as the second component.

6. The mixture of claim 5 in which the hydroxy acid is glycolic acid and the carbohydrate is a disaccharide.

7. The mixture of claim 6 in which the disaccharide is trehalose.

8. The mixture of claim 1 which comprises from about 40 to about 95% by weight of the principal acid component.

9. The mixture of claim 5 which comprises from about 50 to about 90% of a principal acid component.

10. The mixture of claim 6 which comprises from about 50 to about 70% of a principal acid component.

11. A cosmetic or pharmaceutical composition comprising the mixture of claim 1 and a cosmetically or pharmaceutically acceptable carrier.

12. A cosmetic or pharmaceutical composition comprising the mixture of claim 5 and a cosmetically or pharmaceutically acceptable carrier.

13. A cosmetic or pharmaceutical composition comprising the mixture of claim 6 and a cosmetically or pharmaceutically acceptable carrier.

14. A cosmetic or pharmaceutical composition comprising the mixture of claim 9 and a cosmetically or pharmaceutically acceptable carrier.

15. A cosmetic or pharmaceutical composition comprising the mixture of claim 10 and a cosmetically or pharmaceutically acceptable carrier.

16. A method for making a liquid, substantially anhydrous eutectic mixture containing a principal acid component and at least one other component selected from the group consisting of a carbohydrate, a polyol, an amino acid, and a carboxylic acid, the method comprising heating the component having the lowest melting point to the temperature at which it melts, dissolving the remaining component or components in the melted component, and allowing the mixture to cool.

17. The method of claim 16 in which the principal acid component is an alpha hydroxy acid and the other component is a carbohydrate.

18. The method of claim 17 in which the principal acid component is employed in an amount of about 40% to about 95% by weight of the mixture.

19. The method of claim 17 in which the carbohydrate is a monosaccharide, disaccharide, or polysaccharide, and the principal acid component is employed in an amount of from about 50% to about 90% by weight of the mixture.

20. The method of claim 19 in which the carbohydrate is a monosaccharide or disaccharide, and the principal acid component is employed in an amount of from about 50% to about 70% by weight of the mixture.

21. The method of claim 19 in which the principal acid component is glycolic acid and the carbohydrate is trehalose.

22. A eutectic mixture prepared according to the method of claim 16.

23. A eutectic mixture prepared according to the method of claim 17.

24. A eutectic mixture prepared according to the method of claim 18.

25. A eutectic mixture prepared according to the method of claim 19.

26. A eutectic mixture prepared according to the method of claim 20.

27. A eutectic mixture prepared according to the method of claim 21.

28. A cosmetic composition comprising the mixture of claim 22.

29. A cosmetic composition comprising the mixture of claim 23.

30. A cosmetic composition comprising the mixture of claim 24.

31. A cosmetic composition comprising the mixture of claim 25.

32. A cosmetic composition comprising the mixture of claim 26.

33. A cosmetic composition comprising the mixture of claim 27.

* * * * *